United States Patent

Koshimura et al.

[11] Patent Number: 5,223,636
[45] Date of Patent: Jun. 29, 1993

[54] PROCESS FOR PREPARING PARTIALLY ALKOXYLATED POLYSILOXANE

[75] Inventors: Takeo Koshimura; Mikio Endo; Toshinobu Ishihara, all of Jouetsu, Japan

[73] Assignee: Shin-Etsu Chemical Co., Ltd., Tokyo, Japan

[21] Appl. No.: 821,815

[22] Filed: Jan. 17, 1992

[30] Foreign Application Priority Data

Jan. 18, 1991 [JP] Japan ................................. 3-016799

[51] Int. Cl.$^5$ ................................................. C07F 7/18
[52] U.S. Cl. ................................. 556/457; 556/458
[58] Field of Search ............................ 556/457, 458

[56] References Cited

U.S. PATENT DOCUMENTS

| | | | |
|---|---|---|---|
| Re. 29,211 | 5/1977 | Lewis | 556/457 |
| Re. 29,760 | 9/1978 | Brown et al. | 556/457 X |
| 3,320,297 | 5/1967 | Pino | 260/448.8 |
| 3,433,764 | 3/1969 | Walmsley | 556/457 X |
| 3,489,782 | 1/1970 | Pruvost et al. | 556/457 X |
| 3,668,180 | 6/1972 | Brennan et al. | 260/46.5 R |
| 3,792,071 | 2/1974 | Nitzsche et al. | 556/457 |
| 4,209,454 | 6/1980 | Graf et al. | 556/457 |
| 4,261,848 | 4/1981 | Reedy et al. | 556/457 X |
| 4,298,753 | 11/1981 | Schinabeck et al. | 556/457 X |
| 4,506,087 | 3/1985 | Fischer et al. | 556/471 |
| 4,609,752 | 9/1986 | Giesing et al. | 556/457 |

FOREIGN PATENT DOCUMENTS

| | | |
|---|---|---|
| 0032376 | 7/1981 | European Pat. Off. |
| 0107765 | 5/1984 | European Pat. Off. |
| 0167924 | 1/1986 | European Pat. Off. |
| 1044274 | 1/1964 | United Kingdom |

*Primary Examiner*—Paul F. Shaver
*Attorney, Agent, or Firm*—Birch, Stewart, Kolasch & Birch

[57] ABSTRACT

A partially alkoxylated polysiloxane is prepared by using a reactor kettle equipped with a reaction column and a reflux condenser, charging the kettle with a lower alkoxysilane where the kettle liquid is kept boiling, continuously feeding a halogenated lower alkylsilane into the kettle through the column top and continuously feeding a mixture of water and a monohydric alcohol into the kettle in controlled rates, completely alkoxylating the halogenosilane with the alcohol within the column to continuously yield an alkoxysilane, hydrolyzing the alkoxysilane, with the hydrogen halide by-produced during alkoxylation acting as a catalyst, and withdrawing a partially alkoxylated polysiloxane containing less than 5% by weight of the alcohol from the kettle.

14 Claims, 1 Drawing Sheet

PROCESS FOR PREPARING PARTIALLY ALKOXYLATED POLYSILOXANE

This invention relates to a process for preparing a partially alkoxylated polysiloxane of quality suitable as an intermediate for the synthesis of silicone resins.

BACKGROUND OF THE INVENTION

Various methods are known in the prior art for the production of substituted or unsubstituted alkoxysilanes and alkoxypolysiloxanes. U.S. Pat. No. 3,792,071 discloses a continuous process of reacting chlorosilane with a substituted or unsubstituted alcohol and optional water in a reactor column equipped with a reflux condenser and kept at high temperatures. In this process, chlorosilane is admitted into the reaction column through its top and the alcohol in gas form is admitted into the column at or in proximity to its lower end, and water is admitted into the column at any desired position. An intermediate section in the column is kept at a temperature higher by at least 0.5° C. than the boiling point of the alcohol, and excess alcohol boiling under reflux always exists at the column top throughout the reaction. The reaction product is withdrawn from the column through the lower end or from below the alcohol admission inlet.

This process is specially intended for the continuous production of alkoxysilanes. For example, an alkoxysilane is continuously produced by admitting methyltrichlorosilane and gaseous ethanol at 110° C. into a reaction column heated at a temperature of 100° C., thereby effecting reaction between these compounds at high temperatures, allowing a reaction product (alkoxysilane) to exit from the lower end of the column, and separating excess ethanol from the reaction product by distillation.

If it is desired to effect partial hydrolysis of methyltrichlorosilane concurrently in this process, methyltrichlorosilane is admitted as a triol solution and water is introduced as steam at a temperature of 105° C. into the column below the silane inlet. This type of reaction, however, does not yield a well balanced high molecular weight reaction product, but rather a mixture of methylethoxypolysiloxane and methyltriethoxysiloxane. Additionally, the above-mentioned process uses solvent and feeds water in gas form, that is, steam. Such a steam conduit requires intense thermal insulation because otherwise, water can condense intermediate the conduit, failing to provide desired supply of water so that an alkoxysilane having a desired degree of hydrolysis is produced no longer. Also otherwise, gelation can occur in the supply conduit, failing to produce an end product.

U.S. Pat. No. 4,209,454 discloses a process for producing a polysiloxane having a hydrocarbon residue attached to silicon through oxygen by reacting a halogenosilane with alcohol and water in the presence of a desired polysiloxane, characterized by the steps of admitting alcohol, water, and an acidic catalyst capable of promoting condensation of a group to which a Si bond is condensible into a still equipped with a column and optionally, a reflux condenser and previously charged with the desired polysiloxane, in such amounts that there are present at least 5% by weight of the alcohol and 0.001 to 5% by weight of the catalyst based on the total weight of the alcohol, catalyst, and polysiloxane in the still, heating the contents of the still under reflux for boiling, introducing a halogenosilane to be reacted into the column at a position of at least 1 m above the column lower end, and continuously withdrawing the polysiloxane from the still as it is formed.

This process is an improvement over the first-mentioned process. Studying the process, the inventors have found the following problems. Since the alcohol is admitted into the still (or reactor) in such an amount that there is present at least 5% by weight of the alcohol based on the total weight of the alcohol, catalyst, and polysiloxane in the still as mentioned above, the reaction system becomes an alcohol excess system containing at least 5% by weight of alcohol. Then a substantial amount of the alcohol can be left in the reaction system and consequently, a substantial amount of a hydrogen halide by-product resulting from reaction of halogenosilane with alcohol can be left in the resulting polysiloxane. This is probably a result of the extremely high solubility of hydrogen halide in alcohol as compared with the low solubility of hydrogen halide in polysiloxane. In any case, the above-mentioned process becomes complicated since it requires an extra step of distilling off hydrogen halide along with alcohol by stripping, neutralization or the like. The use of a separate catalyst is disadvantageous in economy. There is a need for overcoming these problems.

U.S. Pat. No. 3,668,180 discloses a process for producing an alkoxyorganopolysiloxane comprising the steps of reacting an organohalogenosilane with water and a lower aliphatic alcohol in the presence of a hydrocarbon solvent in a first reactor between −10° C. and +10° C., and continuously introducing the resulting intermediate into a second reactor filled with a supplemental solvent where reaction is completed under reflux. This process also suffers from cumbersome operations associated with the use of solvent and two reactors.

SUMMARY OF THE INVENTION

Therefore, an object of the present invention is to provide a process for preparing a partially alkoxylated polysiloxane of quality in a simple manner with commercial advantages.

Making investigations to achieve this and other objects and to overcome the problems of the prior art, especially the process of U.S. Pat. No. 4,209,454, the inventors arrived at the present invention which provides a process for preparing a partially alkoxylated polysiloxane using an apparatus comprising a reactor kettle equipped with a reaction column and a reflux condenser, comprising the steps of charging the kettle with an alkoxysilane of the general formula (1):

$$R_nSi(OR')_{4-n} \quad (1)$$

wherein R is a hydrogen atom or a substituted or unsubstituted monovalent hydrocarbon group having 1 to 8 carbon atoms, R' is a substituted or unsubstituted monovalent hydrocarbon group having 1 to 8 carbon atoms, and n is an integer of from 0 to 2, where the kettle liquid is kept boiling, continuously feeding a halogenosilane of the general formula (2):

$$R_nSiX_{4-n} \quad (2)$$

wherein X is a chlorine atom or bromine atom, R and n are as defined above, having a molecular weight Xw into the kettle through the top of the column at a rate of a mol/hour, continuously feeding into the kettle a mixture of water at a rate of b mol/hour wherein $0<b<\{a(4-n)\}/2$ and a monohydric alcohol of the general formula (3):

$$R'OH \qquad (3)$$

wherein R' is as defined above, having a molecular weight Yw at a rate of c mol/hour wherein $c=a(4-n)-2b+\alpha$ and $0 \leq \alpha < \{aXw+cYw+18b-36-.5a(4-n)\}/19Yw$, completely alkoxylating the halogenosilane of formula (2) with the alcohol of formula (3) within the column to continuously yield the alkoxysilane of formula (1), hydrolyzing the alkoxysilane of formula (1) with the hydrogen halide by-produced during alkoxylation of the halogenosilane of formula (2) acting as a catalyst, and withdrawing a partially alkoxylated polysiloxane containing less than 5% by weight of the alcohol of formula (3) from the kettle.

In the process of U.S. Pat. No. 4,209,454 referred to above, alcohol, water, and an acidic catalyst are admitted into a still in such amounts that there are present at least 5% by weight of the alcohol and 0.001 to 5% by weight of the catalyst based on the total weight of the alcohol, catalyst, and polysiloxane in the still. Regarding this alcohol excess system containing at least 5% by weight of alcohol in the still or reactor, the inventors found that an end product or partially alkoxylated polysiloxane is withdrawn from the reaction system together with substantial amounts of the alcohol and hydrogen halide. Our further study led to the discovery that reaction can fully proceed even when the amount of alcohol used is reduced to the theoretical amount to completely alkoxylate the halogenosilane, that is, efficient production of alkoxysilane is possible even if the system is not specially designed to be an alcohol excess system. In this regard, the monohydric alcohol resulting from hydrolysis reaction in the reactor kettle and the monohydric alcohol of formula (3) admitted into the reactor kettle from an external source (the total of both the monohydric alcohol portions provides a sufficient amount to completely alkoxylate the halogenosilane) are boiled up from within the reactor kettle on the boil into the reactor column where they react with the halogenosilane of formula (2). The hydrogen halide by-produced during this reaction serves as an acidic catalyst for promoting condensation of a group to which a Si bond is condensible. Consequently, efficient hydrolysis reaction of the halogenosilane takes place to complete alkoxylation without a need to separately add a catalyst from the exterior.

Therefore, in accordance with the present process, since a mixture of water in an amount equal to or in slight excess of the theoretical amount to completely alkoxylate the halogenosilane of formula (2) fed from the column top and the alcohol of formula (3) is fed to the reactor kettle, the presence of a large excess of monohydric alcohol in the kettle is avoided. Since the hydrogen halide by-produced disperses without substantially dissolving in the partially alkoxylated polysiloxane, a step of removing the hydrogen halide as by neutralization is eliminated. These factors restrain any side reaction and facilitate manufacture of a partially alkoxylated polysiloxane having a desired degree of hydrolysis. Additionally, the partially alkoxylated polysiloxane thus obtained contains less than 5% by weight of alcohol or is free of alcohol, and is thus employed as an intermediate for the manufacture of silicone resins without an additional step of removing the alcohol as by distillation. Further, the present invention eliminates a need to supply solvent or gaseous water and hence, the risk of gelation, and a need to add a catalyst from without the system. Therefore, the present process is capable of producing a partially alkoxylated polysiloxane of quality in one pass with many commercial advantages including ease of operation and low cost.

DETAILED DESCRIPTION OF THE INVENTION

Figure 1:
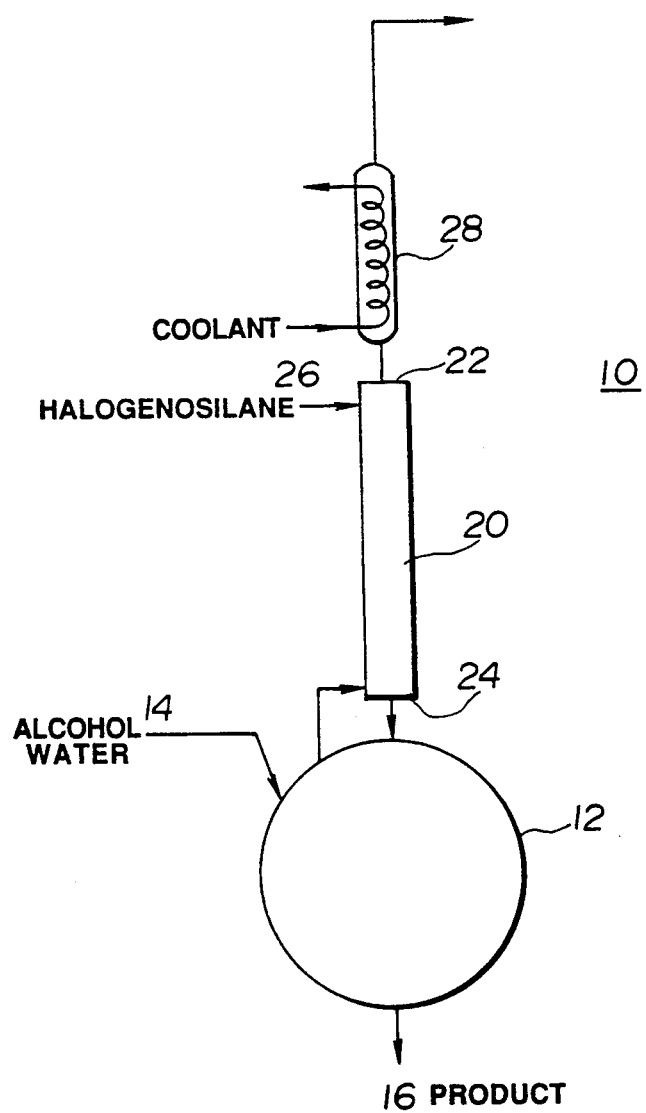
FIG. 1 is a schematic illustration of one exemplary reaction apparatus used in the process of the invention.

The process of the invention starts with a halogenosilane of the general formula (2):

$$R_nSiX_{4-n} \qquad (2)$$

having a molecular weight Xw. In formula (2), R is a hydrogen atom or a substituted or unsubstituted monovalent hydrocarbon group having 1 to 8 carbon atoms, for example, alkyl groups such as methyl, ethyl, propyl, butyl, hexyl, and octyl groups; alkenyl groups such as vinyl and allyl groups; aryl groups such as phenyl, tolyl, and xylyl groups; aralkyl groups such as a benzyl group; and substituted ones of these monovalent hydrocarbon groups in which some or all of the hydrogen atoms are replaced by groups inert to alcohol and water, for example, halogen atoms. X is a chlorine or bromine atom, with chlorine being preferred for commercial availability. Letter n is an integer equal to 0, 1 or 2.

Examples of the halogenosilane of formula (2) include $SiCl_4$, $CH_3SiCl_3$, $(CH_3)_2Cl_2$, $CH_2=CHSiCl_3$, and $C_6H_5—SiCl_3$.

Another starting reactant is a monohydric alcohol of the general formula (3):

$$R'OH \qquad (3)$$

having a molecular weight Yw. In formula (3), R' is a substituted or unsubstituted monovalent hydrocarbon group having 1 to 8 carbon atoms, for example, alkyl groups such as methyl, ethyl, propyl, butyl, hexyl, and octyl groups; alkenyl groups such as vinyl and allyl groups; aryl groups such as phenyl, tolyl, and xylyl groups; aralkyl groups such as a benzyl group; and substituted ones of these monovalent hydrocarbon groups in which some or all of the hydrogen atoms are replaced by groups inert to alcohol and water, for example, halogen atoms.

Examples of the monohydric alcohol include methyl alcohol, ethyl alcohol, isopropyl alcohol, butyl alcohol, amyl alcohol, hexyl alcohol, octyl alcohol, allyl alcohol, and benzyl alcohol. Among these, methyl alcohol, ethyl alcohol, and isopropyl alcohol are preferred for ease of hydrolysis.

Both the halogenosilane of formula (2) and the alcohol of formula (3) may be used alone or in admixture of two or more in any desired proportion.

The process of the invention employs an apparatus comprising a reactor kettle equipped with a reaction column and a reflux condenser. Referring to FIG. 1, the apparatus 10 includes a reactor kettle 12 having an inlet 14 and an outlet 16. The kettle at an upper opening thereof is connected to a cylindrical reaction column 20 having a top 22 and a bottom 24. The column 20 has an inlet line 26 at the top. The column at its top 22 is connected to a reflux condenser 28 through which a coolant line extends. The column is preferably filled with packings such as Raschig rings.

In the practice of the invention, the reactor kettle 12 is first charged with an alkoxysilane of the general formula (1):

$$R_nSi(OR')_{4-n} \qquad (1)$$

wherein R, R', and n are as defined above, which is the same as that resulting from reaction between a halogenosilane of formula (2) and an alcohol of formula (3), whereupon the kettle liquid is kept boiling. Then a halogenosilane of formula (2) is continuously fed from the inlet line 26 into the reactor kettle 12 through the top 22 of the reaction column 20 and a mixture of a monohydric alcohol of formula (3) and water is continuously fed into the reactor kettle 12 directly from the inlet line 14.

At this stage, the halogenosilane of formula (2), monohydric alcohol of formula (3) and water are fed in such proportions that the monohydric alcohol is present in the reactor kettle in an amount equal to or in slight excess of the theoretical amount to completely alkoxylate the halogenosilane of formula (2). More particularly, it is recommended to feed a halogenosilane of formula (2) having a molecular weight Xw at a rate of a mol/hour, water at a rate of b mol/hour, and a monohydric alcohol of formula (3) having a molecular weight Yw at a rate of c mol/hour wherein $$0 < b < \{a(4-n)\}/2,$$

$$c = a(4-n) - 2b + \alpha, \text{ and}$$

$$0 \leq \alpha < \{aXw + cYw + 18b - 36.5a(4-n)\}/19Yw.$$

Water is used in hydrolysis of the alkoxysilane of formula (1) which results from reaction between the halogenosilane of formula (2) and the alcohol of formula (3) in the following scheme.

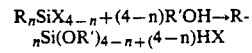

$$R_nSiX_{4-n} + (4-n)R'OH \rightarrow R_nSi(OR')_{4-n} + (4-n)HX$$

Hydrolysis of the alkoxysilane of formula (1) produces R'OH, that is, the alcohol of formula (3) as a by-product, which is repeatedly used in the formation of the alkoxysilane of formula (1). Therefore, the actual amount of the alcohol of formula (3) to be admitted along with water is the theoretical amount minus the amount of alcohol by-produced, that is, the amount of water admitted. In the mathematical expression of the amount of alcohol admitted (c), α represents an excess of alcohol, and c wherein α=0 is the amount needed to completely alkoxylate the halogenosilane admitted.

The amounts of halogenosilane, monohydric alcohol, and water admitted are so limited for the following reason. Reaction of the halogenosilane with the monohydric alcohol produces a hydrogen halide as a by-product which is well soluble in the monohydric alcohol, but sparingly soluble in a partially alkoxylated polysiloxane. If the monohydric alcohol and water are fed in excess, the majority of the hydrogen halide will remain in the partially alkoxylated polysiloxane, which raises some problems including an extra step of neutralization or post treatment required for isolation and side reaction disturbing to provide a partially alkoxylated polysiloxane having a desired degree of hydrolysis. In contrast, by limiting the amount of monohydric alcohol and water admitted such that the monohydric alcohol is present in the reactor kettle in an amount equal to or in slight excess of the theory to completely alkoxylate the halogenosilane, that is, the monohydric alcohol is not present in large excess, the hydrogen halide is allowed to disperse without significantly dissolving in the partially alkoxylated polysiloxane. This avoids the above-mentioned problems and helps obtain a partially alkoxylated polysiloxane having a desired degree of hydrolysis.

In controlling the amounts of halogenosilane, monohydric alcohol, and water admitted, the preferred amount of water admitted is from about 0.1 to about 0.49 mol, especially from about 0.15 to about 0.25 mol per gram atom of the halogen atom attached to Si. With respect to the amount of alcohol admitted (c), its excess factor α is generally in the range:

$$0 \leq \alpha < \{aXw + cYw + 18b - 36.5a(4-n)\}/19Yw,$$

preferably in the range:

$$0 \leq \alpha \leq \{aXw + cYw + 18b - 36.5a(4-n)\}/95Yw.$$

Prior to the onset of reaction, the reactor kettle previously charged with the alkoxysilane should be heated to a temperature at which the kettle liquid is on the boil. This heating allows the hydrogen halide by-produced during reaction of the halogenosilane with the monohydric alcohol to shift into the gas phase quickly. In this regard, if desired, an inert gas may be introduced into the reactor kettle so as to bubble the reaction system, thereby helping the hydrogen halide shift from the reactor kettle to the gas phase and control its concentration in the reactor kettle to a desired range to be described later.

During the progress of reaction, an intermediate section of the reactor column is desirably heated under the pressure prevailing in the column to a temperature at least ⅓° C. higher than the boiling temperature of the alcohol used such that the temperature gradually increases from an upper portion to a lower portion of the column (preferably to establish a temperature difference of about 5° to 10° C. between the column top and bottom). This temperature control prevents a lowering of temperature which otherwise results from the hydrogen halide depriving the surrounding of latent heat for vaporization as it leaves the liquid phase. In addition, the temperature control ensures the takeoff of hydrogen halide in accordance with the boiling point that increases as a halogen atom directly attached to a silicon atom is replaced by an alkoxy group. It is appreciated that pressure need not be applied since reaction can proceed under atmospheric pressure.

In the process of the invention, the hydrogen halide by-produced during the above.mentioned reaction serves as a catalyst for promoting hydrolysis, more specifically an acidic catalyst for promoting condensation of a group to which a Si bond by-produced is condensible. In this regard, the concentration of hydrogen halide in the reactor kettle is preferably controlled to range from about 0.005 to about 0.1% by weight, especially from about 0.01 to about 0.03% by weight of the entire reaction system in the reactor kettle. Concentrations of hydrogen halide of less than 0.005% by weight are too low to completely drive hydrolysis so that SiOH might be left. Concentrations of more than 0.1% by weight would sometimes require neutralization or the like. It is appreciated that the hydrogen halide by-produced will disperse and is not substantially dissolved in an end product or partially alkoxylated polysiloxane.

In this way, the process of the invention yields a partially alkoxylated polysiloxane which contains less than 5% by weight of alcohol because the amounts of alcohol and water admitted are controlled. Therefore, the partially alkoxylated polysiloxane can be utilized as an intermediate for the manufacture of silicone resin or the like without an extra step.

EXAMPLE

Examples of the present invention are given below by way of illustration and not by way of limitation.

EXAMPLE 1

To a reactor kettle having a volume of 1 liter was connected a reaction column having a length of 1 m and an inner diameter of 30 mm and filled with Raschig rings of 5 mm in diameter. A low-temperature condenser cooled with dry ice-methyl alcohol coolant was connected to the column at its top. The kettle was charged with methyltrimethoxysilane and heated for boiling. Then a mixture of 7.2 mol/hour of methyl alcohol and 1.8 mol/hour of water was admitted into the kettle and 3.6 mol/hour of methyltrichlorosilane was admitted into the kettle through the top of the column while methylmethoxypolysiloxane was continuously withdrawn from the kettle. The product taken out assumed a constant composition after about two hours from the start of reactant supply, and continuous operation was conducted for 6 hours since then. During the process, the reaction temperature was 110° C. in the kettle, 70° C. at the bottom, 65° C. at the center, and 60° C. at the top of the column, and the pressure was atmospheric. At the end of reaction, the apparatus was inspected to find no gel. The methylmethoxypolysiloxane product had a silanol content of 0, a methoxy content of 54.9% by weight, a Si content of 24.7% by weight, a HCl content of 120 mg/liter, and a methanol content of 0.5% by weight.

EXAMPLE 2

The same apparatus as in Example 1 was used. The kettle was charged with methyltrimethoxysilane and heated for boiling. Then a mixture of 6.8 mol/hour of methyl alcohol and 2.0 mol/hour of water was admitted into the kettle and 3.6 mol/hour of methyltrichlorosilane was admitted into the kettle through the column top while methylmethoxypolysiloxane was continuously withdrawn from the kettle. The product assumed a constant composition after about two hours from the start of reactant supply, and continuous operation was conducted for 6 hours since then. During the process, the reaction temperature was 118° C. in the kettle, 70° C. at the bottom, 65° C. at the center, and 60° C. at the top of the column, and the pressure was atmospheric. At the end of reaction, the apparatus was inspected to find no gel. The methylmethoxypolysiloxane product had a silanol content of 0, a methoxy content of 53.0% by weight, a Si content of 25.4% by weight, a HCl content of 110 mg/liter, and a methanol content of 0.3% by weight.

EXAMPLE 3

The same apparatus as in Example 1 was used. The kettle was charged with methyltriisopropoxysilane and heated for boiling. Then a mixture of 7.2 mol/hour of isopropyl alcohol and 1.8 mol/hour of water was admitted into the kettle and 3.6 mol/hour of methyltrichlorosilane was admitted into the kettle through the column top while methylisopropoxypolysiloxane was continuously withdrawn from the kettle. The product assumed a constant composition after about two hours from the start of reactant supply, and continuous operation was conducted for 6 hours since then. During the process, the reaction temperature was 185° C. in the kettle, 85° C. at the bottom, 80° C. at the center, and 75° C. at the top of the column, and the pressure was atmospheric. At the end of reaction, the apparatus was inspected to find no gel. The methylisopropoxypolysiloxane product had a silanol content of 0, an isopropoxy content of 69.9% by weight, a Si content of 16.5% by weight, a HCl content of 350 mg/liter, and an isopropyl alcohol content of 0.8% by weight.

COMPARATIVE EXAMPLE 1

The same apparatus as in Example 1 was used. To the kettle were admitted 7.2 mol/hour of methyl alcohol and 1.8 mcl/hour of water in gas form through the bottom of the column and 3.6 mcl/hour of methyltrichlorosilane through the column top. The methyl alcohol/water supply conduit was heated at 110° C., but condensation occurred at the inlet to the column to form a gel which clogged the conduit, disabling continuous operation.

COMPARATIVE EXAMPLE 2

The same apparatus as in Example 1 was used. A mixture of 9.2 mol/hour of methyl alcohol and 1.8 mol/hour of water was admitted into the kettle and 3.6 mol/hour of methyltrichlorosilane was admitted into the kettle through the column top. The methylmethoxypolysiloxane obtained had a methoxy content of 48.8% by weight and a Si content of 28.8% by weight outside a desired degree of hydrolysis. Hydrolysis proceeded beyond the desired degree of hydrolysis because methyl alcohol reacted with HCl in the kettle to form $CH_3Cl$ and $H_2O$. The product had a methyl alcohol content of 19.8% by weight and a HCl content of 1600 mg/liter. The methylmethoxypolysiloxane was collected by distilling off methyl alcohol and HCl.

There has been described a process for preparing a partially alkoxylated polysiloxane which has a number of operational and economic benefits including ease of operation, elimination of extra steps like neutralization of by-products and isolation of the end product by distillation, and elimination of a separate catalyst. The process is thus quite advantageous in industrial application. The partially alkoxylated polysiloxane obtained by the process is of high quality as shown by an alcohol content of less than 5% by weight and thus widely utilizable without isolation as an intermediate for the manufacture of silicone resins or the like.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing a partially alkoxylated polysiloxane using an apparatus comprising a reactor kettle equipped with a reaction column and a reflux condenser, comprising the steps of charging the reactor kettle with an alkoxysilane of the general formula (1):

$$R_nSi(OR')_{4-n} \qquad (1)$$

wherein R is a hydrogen atom or a substituted or unsubstituted monovalent hydrocarbon group having 1 to 8 carbon atoms, R' is a substituted or unsubstituted monovalent hydrocarbon group having 1 to 8 carbon atoms, and n is an integer of from 0 to 2, where the kettle liquid is kept boiling, continuously feeding a halogenosilane of the general formula (2):

$$R_nSiX_{4-n} \qquad (2)$$

wherein X is a chlorine atom, R and n are as defined above, having a molecular weight Xw into the kettle through the top of the column at a rate of a mol/hour and continuously feeding into the kettle a mixture of water at a rate of b mol/hour wherein $0<b<\{a(4-n)\}/2$ and a monohydric alcohol of the general formula (3):

$$R'OH \qquad (3)$$

wherein R' is as defined above, having a molecular weight Yw at a rate of c mol/hour wherein $c=a(4-n)-2b+\alpha$ and $0\leq\alpha<\{aXw+cYw+18b-36.5a(4-n)\}/19Yw$, completely alkoxylating the halogenosilane of formula (2) with the alcohol of formula (3) within the column to continuously yield the alkoxysilane of formula (1), hydrolyzing the alkoxysilane of formula (1) with the hydrogen halide by-produced during alkoxylation of the halogenosilane of formula (2) acting as a catalyst, and withdrawing a partially alkoxylated polysiloxane containing less than 5% by weight of the alcohol of formula (3) from the kettle.

2. The process of claim 1 which further comprises heating an intermediate section of the reaction column to a temperature at least ½° C. higher than the boiling temperature of the alcohol used such that the temperature gradually increases from the top to the bottom of the column.

3. The process of claim 1 which further comprises controlling the concentration of the hydrogen halide to about 0.005 to about 0.1% by weight in the reactor kettle.

4. The process of claim 1, wherein R in the halogenosilane of formula (2) is a member selected from the group consisting of methyl, ethyl, propyl, hexyl, octyl, vinyl, allyl, phenyl, tolyl, xylyl, benzyl, and a member of this group substituted with one or more halogen atoms.

5. The process of claim 1, wherein the halogenosilane of formula (2) is selected from the group consisting of $SiCl_4$, $CH_3SiCl_3$, $(CH_3)_2Cl_2$, $CH_2=CHSiCl_3$ and $C_6H_5—SiCl_3$.

6. The process of claim 1, wherein R' in the monohydric alcohol of formula (3) is a member selected form the group consisting of methyl, ethyl, propyl, hexyl, octyl, vinyl, allyl, phenyl, tolyl, xylyl, benzyl, and a member of this group substituted with one or more halogen atoms.

7. The process of claim 1, wherein the monohydric alcohol of formula (3) is a member selected form the group consisting of methyl alcohol, ethyl alcohol, isopropyl alcohol, butyl alcohol, amyl alcohol, hexyl alcohol, octyl alcohol, allyl alcohol, and benzyl alcohol.

8. The process of claim 1, wherein the monohydric alcohol of formula (3) is methyl alcohol, ethyl alcohol or isopropyl alcohol.

9. The process of claim 1, wherein the halogenosilane of formula (2) is selected form the group consisting of $SiCl_4$, $CH_3SiCl_3$, $(CH_3)_2Cl_2$, $CH_2=CHSiCl_3$ and $C_6H_5—SiCl_3$; and wherein the monohydric alcohol of formula (3) is methyl alcohol, ethyl alcohol or isopropyl alcohol.

10. The process of claim 1, wherein the water is admitted in an amount of from about 0.1 to 0.49 mol per gram atom of halogen attached to Si in the halogenosilane of formula (2).

11. The process of claim 1, wherein the water is admitted in an amount of from about 0.15 to 0.25 mol per gram atom of halogen attached to Si in the halogenosilane of formula (2).

12. The process of claim 1, wherein the excess factor $\alpha$ for the amount of the monohydric alcohol of formula (3) admitted is in the range $0\leq\alpha\leq\{aXw+cYw+18b-36.5a(4-n)\}/95Yw$.

13. The process of claim 2, wherein the temperature gradually increases from the top to the bottom of the column about 5° and 10° C.

14. The process of claim 1, which further comprises controlling the concentration of the hydrogen halide to about 0.005 to about 0.1% by weight in the reactor kettle.

* * * * *